(12) United States Patent
Kaiser et al.

(10) Patent No.: US 6,501,825 B2
(45) Date of Patent: Dec. 31, 2002

(54) METHODS FOR IDENTIFICATION AND VERIFICATION

(75) Inventors: Bruce J. Kaiser, St. Louis, MO (US); Gerhard A. Meyer, Worthington, OH (US)

(73) Assignee: KeyMaster Technologies, Inc., Kennewick, WA (US)

( * ) Notice: Subject to any disclaimer, the term of this patent is extended or adjusted under 35 U.S.C. 154(b) by 0 days.

(21) Appl. No.: 09/766,542

(22) Filed: Jan. 19, 2001

(65) Prior Publication Data
US 2002/0097832 A1 Jul. 25, 2002

(51) Int. Cl.[7] ............................................. G01N 23/223
(52) U.S. Cl. .............................................. 378/45; 378/44
(58) Field of Search ............................. 378/44, 45, 47, 378/48, 50

(56) References Cited

U.S. PATENT DOCUMENTS

| | | |
|---|---|---|
| 4,045,676 A | 8/1977 | Rolle |
| 4,136,778 A * | 1/1979 | Wortman et al. ............ 209/576 |
| 4,251,726 A | 2/1981 | Alvarez |
| 4,363,965 A | 12/1982 | Soberman et al. |
| 4,390,452 A | 6/1983 | Stevens |
| 4,445,225 A * | 4/1984 | White ......................... 235/491 |
| 4,476,382 A | 10/1984 | White |
| 4,485,308 A * | 11/1984 | Rabatin ....................... 250/271 |
| 4,767,205 A | 8/1988 | Schwartz et al. |
| 4,862,143 A | 8/1989 | Hirshfield et al. |
| 5,057,268 A | 10/1991 | Muller |
| 5,185,773 A | 2/1993 | Blossfeld et al. |
| 5,208,630 A | 5/1993 | Goodbrand et al. |
| 5,301,044 A | 4/1994 | Wright |
| 5,461,654 A | 10/1995 | Grodzins et al. |
| 5,474,937 A | 12/1995 | Anderson, II et al. |
| 5,527,707 A | 6/1996 | Fukazawa |
| 5,677,187 A | 10/1997 | Anderson, II et al. |
| 5,760,394 A | 6/1998 | Welle |
| 5,849,590 A | 12/1998 | Anderson, II et al. |
| 6,005,915 A | 12/1999 | Hossain et al. |
| 6,007,744 A | 12/1999 | Nacker |
| 6,025,200 A | 2/2000 | Kaish et al. |
| 6,030,657 A | 2/2000 | Butland et al. |
| 6,041,095 A | 3/2000 | Yokhin |
| 6,075,839 A | 6/2000 | Treseder |
| 6,097,785 A | 8/2000 | Elam |
| 6,111,929 A | 8/2000 | Hazlett |
| 6,130,931 A | 10/2000 | Laurila et al. |
| 6,165,609 A * | 12/2000 | Curatolo ..................... 250/365 |
| 6,178,226 B1 | 1/2001 | Hell et al. |

FOREIGN PATENT DOCUMENTS

| | | |
|---|---|---|
| EP | 0 911 626 A1 | 10/1998 |
| EP | 0 911 627 A1 | 10/1998 |

* cited by examiner

*Primary Examiner*—Robert H. Kim
*Assistant Examiner*—Hoon K. Song
(74) *Attorney, Agent, or Firm*—Kenneth E. Horton; Rader, Fishman & Grauer PLLC (57) ABSTRACT

Secure documents and methods and apparatus for making the same. The documents are made secure using apparatus and methods in which one or more taggants are placed in the paper or ink of the document. The present or absence of the taggant within the document is detected by x-ray fluorescence analysis, thereby identifying or verifying the document.

44 Claims, 7 Drawing Sheets

METHODS FOR IDENTIFICATION AND VERIFICATION

FIELD OF THE INVENTION

The present invention generally relates to apparatus and methods for identification and verification. More particularly, the present invention relates to apparatus and methods for detecting an element or compound intrinsically present—or extrinsically added—in an article or product by using X-ray fluorescence to identify and verify that article or product. Even more particularly, the present invention relates to secure documents and methods and apparatus for making the same.

BACKGROUND OF THE INVENTION

There has been significant interest in apparatus and methods for identifying and verifying various articles or products such as explosives, ammunition, paint, petroleum products, and documents. Known methods used to identify and verify generally involve adding and detecting materials like code-bearing microparticles, bulk chemical substances, and radioactive substances. Other methods used for identifying and verifying articles include those described in U.S. Pat. Nos. 6,030,657, 6,024,200, 6,007,744, 6,005,915, 5,849,590, 5,760,394, 5,677,187, 5,474,937, 5,301,044, 5,208,630, 5,057,268, 4,862,143, 4,390,452, 4,363,965, and 4,045,676, as well as European Patent Application Nos. 0911626 and 0911627, the disclosures of which are incorporated herein by reference.

It is also known to apply materials to articles in order to track, for example, point of origin, authenticity, and their distribution. In one method, inks which are transparent in visible light are sometimes applied to materials and the presence (or absence) of the ink is revealed by ultraviolet or infrared fluorescence. Other methods include implanting microscopic additives that can be detected optically. However, detecting these materials is primarily based on optical or photometric measurements.

Unfortunately, many of the apparatus and methods for identifying and verifying articles using such materials (called taggants) are unsatisfactory for several reasons. First, they are often difficult and time-consuming. In many instances, a sample of the article must be sent to an off-site laboratory for analysis. In other instances, the apparatus are often expensive, large, and difficult to operate. In yet other instances, the taggant used is radioactive, causing serious health concerns.

The known apparatus and methods for identification and verification are also unsatisfactory because they require a "line-of-sight" analysis method. This line of sight requirement entails that the apparatus must be able to "see" the taggant in order to detect it. This can be detracting when it would be desirable to detect the taggant without having to see the taggant, e.g., such as when the taggant is located in the middle of large package with packaging and labels "covering" the taggant.

SUMMARY OF THE INVENTION

The present invention provides an apparatus and method in which one or more taggants that are intrinsically located—or extrinsically placed—in an article or product are detected by x-ray fluorescence analysis to identify or verify the article or its point of manufacture. The taggant is manufactured as part of the article or the taggant is placed into a coating, packaging, label, or otherwise embedded within the article for the purpose of later verifying the presence or absence of these elements by x-ray fluorescence to determine the unique elemental composition of the taggant within these articles.

By using x-ray fluorescence analysis, the apparatus and methods of the present invention are simple and easy to use, as well as provide detection by a non line-of-sight method to establish the origin of materials, point of manufacture, authenticity, verification, or product security. The present invention is extremely advantageous because it is difficult to replicate, simulate, alter, transpose, or tamper with. Further, it can be easily recognized by a user in either overt or covert form, easily verified by a manufacturer or issuer, and easily applied to various forms of media in the articles.

BRIEF DESCRIPTION OF THE DRAWINGS

FIGS. 1, 2a, 2b, 3, 4a, 4b, and 5–7 presented in conjunction with this description are views of only particular—rather than complete—portions of apparatus and methods for identification and verification.

DETAILED DESCRIPTION OF THE INVENTION

The following description provides specific details in order to provide a thorough understanding of the present invention. The skilled artisan would understand, however, that the present invention can be practiced without employing these specific details. Indeed, the present invention can be practiced by modifying the illustrated apparatus and method and can be used in conjunction with apparatus and techniques conventionally used in the industry. For example, the present invention is described with respect to paper documents printed from a computer, and methods and apparatus process for printing such documents. But a skilled artisan could easily adapt the present invention for other paper documents and their associated processes and apparatus for printing, such as paper documents from a copiers, facsimiles, plotters, scanners, and any printing press.

The present invention uses x-ray fluorescence analysis to detect at least one taggant intrinsically or extrinsically present in the material of a product or article. With x-ray fluorescence (XRF) analysis, x-rays produced from electron shifts in the inner shell(s) of atoms of the taggants and, therefore, are not affected by the form (chemical bonding) of the article being analyzed. The x-rays emitted from each element bear a specific and unique spectral signature, allowing one to determine whether that specific taggant is present in the product or article.

Figures 1, 2A, 2B:
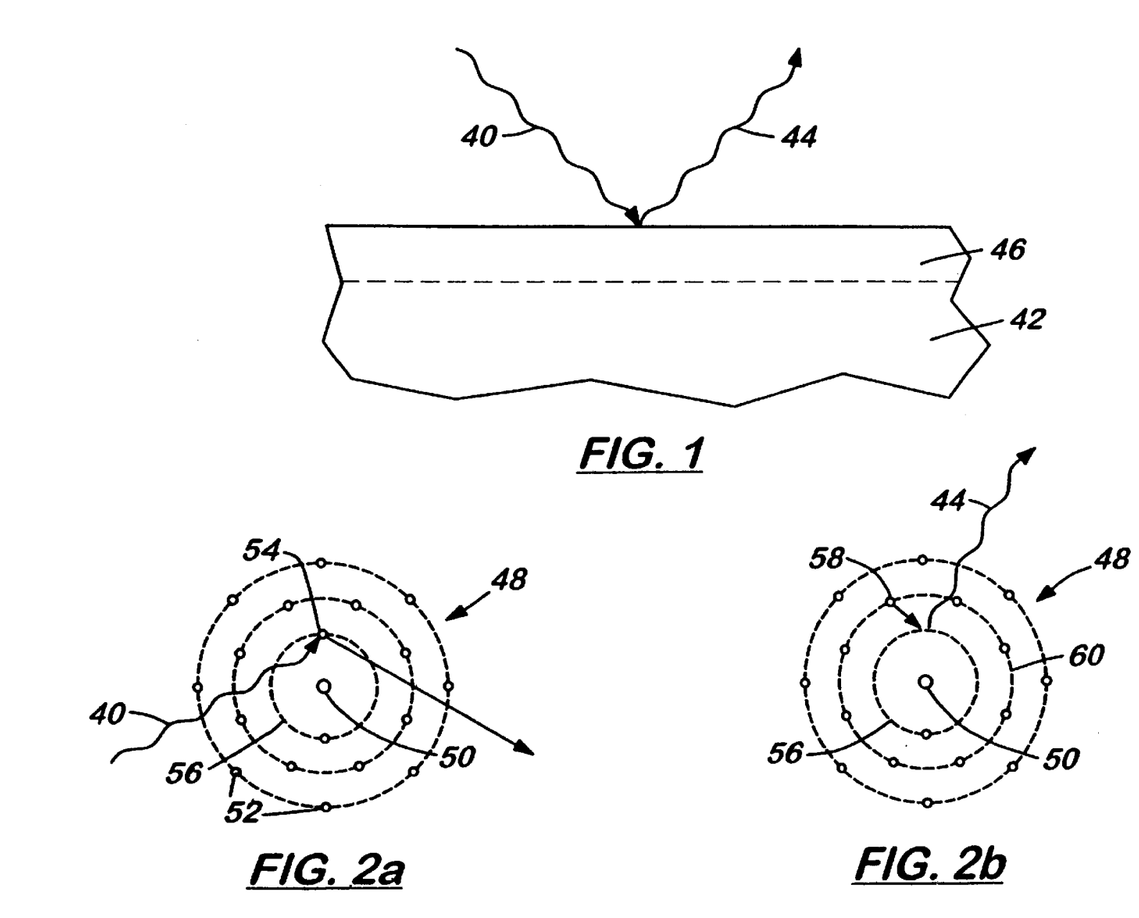
FIGS. 1, 2a, 2b, 3, 4a, 4b, and 5–7 are views of apparatus and methods for identification and verification according to the present invention.

FIGS. 1, 2a, and 2b represent how it is believed XRF generally operates. In FIG. 1, primary gamma rays or x-rays 40 are irradiated on a sample of a target material 46 of article 42. Secondary x-rays 44 are emitted from that sample of target material 46.

In FIGS. 2a and 2b, atom 48 of a taggant located within target material 46 has nucleus 50 surrounded by electrons 52 at discrete distances from nucleus 50 (called electron shells). Each electron shell has a binding energy level equal to the amount of energy required to remove that electron from its corresponding shell. The innermost shell is the K shell, and has the highest binding energy level associated with it. Electron 54 is located within K shell 56.

Primary x-ray or gamma ray photon 40 impacting atom 48 has a given energy. If that energy is greater than the binding energy level of K shell 56, the energy of x-ray photon 40 is absorbed by atom 48, and one of the electrons in K shell 56 (i.e., electron 54) is ejected. With a vacancy now in K shell 56 left by electron 54, atom 48 is energetic and unstable. To become more stable, that vacancy in K shell 56 can be—and usually is—filled by an electron located in a shell with a lower binding energy level, such as L-shell electron 58 in L shell 60. As L-shell electron 58 fills the vacancy in K shell 56, atom 48 emits a secondary x-ray photon 44. The energy levels (or corresponding wavelengths) of such secondary x-ray photons are uniquely characteristic to each taggant, allowing the presence or absence of any specific taggant to be determined.

The at least one taggant can be intrinsically or extrinsically present in the product to be detected (the "target material"). When the taggant(s) is intrinsically present, it is a component (either as an element, compound, or other type of composition) in at least one portion of that target material. When the taggant(s) is extrinsically present, it can be added, incorporated, or inserted into the target material as described below.

The at least one taggant employed in the present invention can be any suitable taggant known in the art. See, for example, U.S. Pat. Nos. 5,474,937, 5,760,394, and 6,025,200, the disclosures of which are incorporated herein by reference. Suitable taggants include any element or compound which is capable of being detected via XRF. The type of elements that can be used as the taggant are theoretically any of those listed in the periodic table, but the lower energy emitted by electrons in the lower atomic-number elements could be a limiting factor. Such lower energies can be re-absorbed much easier into its own material matrix or, in some cases, into the ambient atmosphere (e.g, air). Further, different isotopes of an element, as well as elements which "excite" only under certain conditions could be employed as the taggant in the present invention. Example of taggants that could be used in the present invention include any element with an atomic number ranging from 6 to 94. Preferably, any element above iron on the periodic element, yet within the above range, can be used as the at least one taggant in the present invention. More preferably, any transition elements between germanium and silver can be used as the at least one taggant in the present invention.

The type of taggant depends, among other things, on the target material in which it is located. The target material can interfere with the XRF detection because, as described below, backscattering and peaks emitted by the composition of the target material during XRF analysis can interfere with the taggant peaks. For example, if paper contained an As taggant and trace amounts of Pb existed in the paper, the K-level electrons of As and L-level electrons of Pb could give confusing readings during XRF detection.

In one aspect of the invention, the type of taggant should be selected based on the ability of the taggant and/or the substance in which it is located (i.e., a coating) to attach or bond to the target material. In many instances, the target material will be used, handled, and/or washed extensively. If the taggant (or the substance in which is located) is removed from the target material under such conditions, tagging the target material is of little value. For example, if a film or coating (e.g., ink) containing a taggant is applied to a target material (e.g., paper), the taggant and coating should be selected so that they will not be removed by the conditions to which the target material is periodically subjected (e.g., extensive contact with hands). Preferably, the coating and/or the taggant is selected in this aspect of the invention so that it chemically attaches or bonds to the target material, like paint attaches and bonds with a wall.

In another aspect of the invention, the type of taggant can be selected based on the ability of the taggant and/or the substance in which it is located, such as a coating, to be removed from the target material. In many instances, the purpose for which the target material is tagged will be temporary. After this purpose is completed, the taggant is no longer needed and can optionally be removed. For example, if an identifying film or coating containing a taggant is applied to a target material, once the target material has been identified, the identifying film of coating may no longer be needed and can be removed by suitable means. Preferably, the coating and/or the taggant is selected in this aspect of the invention so that it is removable by mechanical or chemical means.

The amount and concentration of the taggant in the target material can also vary depending on the number of elements used and energy needed. The amount of taggant employed in the present invention is determined by the minimum amount needed for XRF detection. Additional amounts of taggant can be used as described below. The concentration of the taggant is at least about 1 part per million (ppm), and can range from about 1–100 ppm. Larger taggant amounts can be used, but for economic reasons, a small amount is sufficient. Even lower taggant concentrations can be used (i.e, less than 1 ppm) as improved XRF devices and techniques become available.

The form of the taggant in the target material can also vary. The form can be any compound (i.e., salt) or molecule—either small or large—containing the element that is added by itself or with other components. Indeed, the taggant can be combined with various components and/or additives to make a mixture and/or solution. These other components or additives can be selected for various purposes, e.g., to modify the XRF properties, to modify the ability to be inserted into an article/product, to stabilize the mixture or solution, or other purpose known in the chemical arts.

In one aspect of the invention, the at least one taggant is a combination or plurality of taggants. A plurality of taggants could include more than one taggant of the same type, e.g., the same element or compound. A combination of taggants could also be more than one type of taggant, e.g., a different element or compound in different media. For example, a taggant can be dispersed in ink that has been placed on paper that also contains the same or different taggant. The plurality of taggants could also include a combination of at least one intrinsic and at least one extrinsic taggant.

The at least one taggant incorporated in the target material can provide a distinctive code. Such a code could be based on the number and types of taggants present or absent, an abundance ratio (i.e., concentrations) of the same or different taggants, the location of the taggants within the material (i.e., a barcode made of a series of taggants with a space, where the space could be part of the code), the presence of multiple types or forms of a single taggant, or a combination thereof.

As one example of such a code, the present invention can include a system in which the concentration of one taggant in a targeted material is controlled to provide a distinctive code. For example, for tagging ten commercially prepared batches of carpeting, the taggant yttrium oxide can be used. Ten unique codes could then be created for these ten batches by preparing samples of the target material containing various concentrations (i.e., 10 ppm, 20 ppm, . . . 100 ppm) of that taggant.

The number of unique codes available with the use of just a single taggant depends on the precision with which that concentration can be controlled and measured in the sample. For example, if techniques allow concentrations in about 10 ppm increments, 10 unique codes (i.e., 10 ppm, 20 ppm, . . . 100 ppm) can readily be constructed from a single taggant for that concentration range. Additional codes could be created for larger concentration ranges, e.g., 100 codes of a concentration ranging from 10 ppm to 1000 ppm in 10 ppm increments. With the advent of superior concentration and detection techniques (e.g, for smaller increments), more codes may be constructed.

Further, the number of unique codes can be increased by adding additional types and concentrations of the same or different taggants. A significant increase in the number of possible codes can be achieved by using more than one taggant in creating the code. For example, the code can be expanded by adding another taggant with its own specific concentrations. The number of codes can be further expanded by adding a third taggant with its own specific concentrations. Additional taggants could be used to provide even more codes. This coding system depends on the concentration increments of each of the taggants.

The number of codes available in the coding system could also be increased by varying the location of the taggant(s) within the material to be detected. For example, the detected material could be divided into any number of portions (i.e., quadrants) with certain taggants (or codes) being placed in certain of those portions, and optionally not in others, to signify additional information during the XRF analysis.

When taggants include elements or compounds that may be found in the target material or in the environment to which the target material may be exposed, taggant contamination may occur and possibly render the taggant code difficult to read. For example, if a taggant comprising titanium oxide is located in carpet as the targeted material, it is possible that additional amounts of the taggant(s) could be present in the targeted material as a result of environmental contamination, an internal chemical reaction, or other contamination. If this contamination occurs, there will be a change in the concentration of that taggant in the target material. Subsequent measurement of this taggant could yield a value corresponding to an incorrect code.

In such an instance, it is difficult to determine what amount of the taggant present in the targeted material is "contamination" as opposed to taggant present before contamination. This problem can be solved in target materials for which contamination might be suspected by using a backup (i.e., duplicate or otherwise) or secondary system, such as a backup or secondary taggant(s), backup or secondary code, or backup or secondary location. See, for example, the description in U.S. Pat. No. 5,760,394, the disclosure of which is incorporated herein by reference. If desired, more than one such backup or secondary system can be used. The backup or secondary system can also be used for other purposes, e.g., to verify the original coding system.

Any suitable target material can be employed in the present invention. Suitable target materials include those which intrinsically contain the desired taggant(s) or in which the desired taggant(s) can be incorporated. Because XRF detection measures changes in the inner shell(s) of the taggant, it will not be significantly modified by chemical reactions that normally occur in the outer shells. Thus, it is possible to tag chemicals and have the taggant code be carried in any product manufactured with those chemicals. Target materials should be comprised of a material in which XRF detection is easy, e.g., little chance of background contamination, taggant deterioration, taggant destruction, contamination, or other deteriorating condition.

Example of suitable target materials include: paper products like documents, currency, or tickets; solid products like jewelry, carpets, packaging (films, labels, and adhesives), metals, rubbers (tires), woods, or plastics (credit cards); liquid products like lubricating fluids, resins, sprays, paints, oils, inks; hazardous wastes; drugs or pharmaceuticals; gaseous products; or combinations or hybrids of these materials. Additionally, suitable target materials—such as paper documents, drugs, or counterfeit manufactured items—include those that will be subsequently changed. For example, a target material that is suspected might be destroyed could be tagged with elements known to be present in the residue from the destruction. Since the taggant is not usually changed by the chemical process in destruction, a connection between the target material and its residue could be established after destruction. Preferably, the target material of the present invention is printed paper documents.

The target materials containing the at least one taggant can be used for a wide number of applications. For example, tagging paints would allow any article coated with that paint to be identified. In another example, tagging paper and ink used in the paper (or applied to the paper) can be used to establish the authenticity of documents and currency. In yet another example, many manufactured items prone to counterfeiting or theft could benefit from tagging. Tagged threads in clothing could be used to encode information about the date, time, and place of manufacture. Tagging the bulk materials used in the manufacture of such items as compact discs, computer disks, video tapes, audio tapes, electronic circuits, and other items would be useful in tracing and prosecuting theft and counterfeiting cases involving these items.

In the present invention, the at least one taggant can be incorporated into the target material in any suitable form. Suitable forms include those which place that taggant in the target material with little to no damage (either chemical or physical) to the target material. See, for example, the description in U.S. Pat. Nos. 5,208,630, 5,760,394, and 6,030,657, the disclosures of which are incorporated herein by reference. Other suitable forms include using materials containing the taggant such as particulates like microparticles; solvents; coatings and films; adhesives; sprays; or a hybrid or combination of these methods. In any of these forms, the at least one taggant can be incorporated by itself or with another agent.

The at least one taggant can be incorporated in the target material using any suitable technique. Many existing tagging techniques involve the use of microparticles containing the elements, or compounds or compositions of the elements, comprising the at least one taggant. Additionally, particles can be manufactured wherein smaller particles, or compounds or compositions of the elements, containing the taggant. Such particles could be made of: magnetic or fluorescent materials to facilitate collection; refractory materials to enhance particle survival in an explosion; or chemically inert materials to enhance particle survival in a chemical reaction. Indeed, such particles could be made of non-durable, soluble, or reactive materials to enhance taggant dispersal in a fluid, aerosol, or powder system.

When the target material is a liquid article like paints or inks, or adhesives, or has a liquid component, the at least one taggant can be incorporated as an element or compound in solution with the liquid. Thus, the at least one taggant can be incorporated in elemental or compound form either in solution or suspension in the target material. The at least one taggant could also be dissolved or suspended in a solvent used in making the target material so that when that solvent evaporates, the residue left behind would contain the at least one taggant.

The taggant can be inserted into the target material of an article either during or after the article (or a part thereof) has been manufactured. The taggant can be manufactured as a component of the article or as part of a component of the article. During manufacture, the at least one taggant can also be incorporated into another material which comprises part of the target material. Indeed, the at least one taggant could also be an element or compound of the target material itself. The taggant can be incorporated into any location (including surfaces) of the article. Two (and three) dimensional shapes and patterns of the at least one taggant can be constructed using any desired combination of types and numbers of taggants.

The at least one taggant could also be incorporated after manufacture of the target material of the article. The at least one taggant could be incorporated into the already formed target material as a dopant. Additionally, the taggant can be implanted into the article or deposited as a coating or film on the article. As a coating or film, the at least one taggant could be physically or chemically deposited by itself. The at least one taggant could also be incorporated as one ingredient (or contaminant) of another material (such as a mixture or solution) which forms a coating or film. In this aspect of the invention, the at least one taggant can be incorporated as an element or compound in solution (or suspension) with a liquid which is applied, such as by spraying, to the article. For example, the at least one taggant could be dissolved or suspended in a solvent so that when that solvent evaporates after being applied to the article, the residue left behind would contain the at least one taggant.

As apparent from the description above, the present invention has the ability to easily tag small batches of target materials with a code unique to that batch. This can be done manually or in an automated system where each batch (or select batches) of the target material receives a different code. For example, 1000 (or 100) compact discs could be manufacture and each could be tagged with a code of a number from 1 to 1000 (or 1 to 100). Economic and processing considerations, however, might limit the minimum size of each batch and the number of batches that could be tagged.

In one aspect of the invention, the present invention can be incorporated into a process for printing a document from a computer (i.e., digital printing), as well as the document printed by such a process. All printed output from a computer is technically digital. However, the term digital printing refers more to printing finished pages on the computer in contrast to using an offset printing press and commercial printer. Digital printing eliminates numerous mechanical steps present in the conventional printing process (such as newspaper and magazine presses), including making films, color proofs, manually stripping the pieces together, making plates and running the paper through the press four or five times.

For computers, a printer is an output device that accepts text and graphic output from the computer—whether stand-alone or part of a network of computers (like the Internet)—and transfers the information to paper, usually to standard size sheets of paper. Computer printers can generally be distinguished as impact or non-impact printers. Impact printers operate similar an automatic typewriter, with a key or other apparatus striking an inked impression on paper for each printed character. With non-impact printers, the ink is applied to the paper without any such impact. Examples of impact printers include the dot-matrix (serial dot, line dot, and dot band), drum, character, serial, as well as band, chain and train printers.

Examples of non-impact printing include electrophotographic (laser and LED), electrosensitive, electrostatic, ink jet (including IRIS printers which can print on fabric), ionographic, magnetographic, direct thermal, thermal wax transfer, dye sublimation, solid ink, and electron beam imaging. Perhaps the best-known non-impact printers are the inkjet printer, which sprays ink from an ink cartridge at very close range to the paper as it rolls by, and the laser printer, which uses a laser beam reflected from a mirror to attract ink (called toner) to selected paper areas as a sheet rolls over a drum. If desired, some of these printers can be made to print colors by using ink cartridges that contain colors.

The taggant can be incorporated into the printed document in any suitable manner. In one aspect of the invention, the taggant is incorporated into the paper or document before the printing process by manufacturing the paper with the taggant or by incorporating the taggant (such as, by coating) after the paper is made. In another aspect of the invention, the taggant is incorporated into the ink in the printer. When the printer prints the document, the taggant is applied to the paper document along with the ink.

For example, when using a laser printer, the taggant can be incorporated into the ink cartridge either by manufacturing the cartridge with the taggant as a component of the ink or by later adding the taggant to the ink and then mixing until a homogenous mixture is obtained. In the latter instance, the taggant is preferably a powder that is of a finer consistency that the ink powder. When the laser printer prints the document, the ink (along with the taggant) is applied to the paper, thereby creating the paper document with a taggant contained in the ink.

This aspect of the invention could be applied to printers other than just the laser printer in a similar manner, e.g., by incorporating the taggant into the ink source (such as a ribbon). For example, with ink-jet printers, the taggant could be incorporated into the ink by bonding the taggant to the ink. This bonding would be required because of the differences between the inks used in laser printers and the inks used in ink-jet printers. In a similar manner, this aspect of the invention could be used in color printers by incorporated the taggant with the color ink.

The resulting printed document would contain the taggant in the ink which has been applied to the paper. In one aspect of the invention, a single taggant could be present in the ink that has been printed on the paper. In another aspect of the invention, a plurality of taggants could be present in the printed ink by incorporating a plurality of taggants in a single ink source (i.e., cartridge) or by incorporating taggant (s) in a plurality of different ink cartridges.

In one aspect of the invention, a single taggant is present in a consistent concentration in all of the ink. In another aspect, however, the taggant concentration could be varied by using different cartridges with different taggant concentrations and varying the respective amounts of taggant-containing ink while printing. For example, a first ink cartridge (or first portion of a cartridge) could contain a first taggant concentration (ranging from 0% to 100%) and a second cartridge (or second portions of a cartridge) could contain a second taggant concentration (ranging from 100% to 0%). When printing, the taggant concentration in the printed ink could be changed by modifying the respective amount(s) of ink being printed from the first and second cartridges (or portions).

In another aspect of the invention, the taggant can be incorporated into color printing. In a color printing apparatus, a plurality of primary colors (i.e., yellow, cyan, and magenta) are superimposed to produce a desired color, thus providing for a variety of colored images. These colors are produced using various inorganic pigments that are mixed with the ink powder. Black ink has often been used with the above three colors to produce images with enhanced properties, such as additional brightness, as well as to print particularly solid black portions in images. The different colors of ink can come from different cartridges of from different portions (or reservoirs) within the same cartridge. Different taggants could be incorporated into the different colors to produce a printed, color ink containing the taggant(s) in the desired concentration(s).

The present invention could be used for any document containing ink and method for making the same. For example, the present invention could be used for any apparatus which produces a printed document by applying ink from a source (or reservoir) to paper. In particular, the present invention could be used in facsimile apparatus, as well as copiers.

The present invention could also used for documents other than just conventional paper. For example, the present invention could be used to make tickets or any other document that can be printed using the apparatus mentioned above.

Once the paper or document has been printed with the ink containing the taggant(s), the presence, concentration, and location of the taggant(s) can be detected and analyzed for the various purposes mentioned above. For example, the taggant in the printed ink of the document could be detected and analyzed to determine the authenticity of the document.

After the at least one taggant is extrinsically or intrinsically present in the target material(s), the taggant(s) is detected to identify or verify the target material using XRF analysis as illustrated in FIG. 1. Primary x-rays 40 are used to excite a sample of the target material 46, and the secondary x-rays 44 that are emitted by the sample are detected and analyzed.

Figure 3:
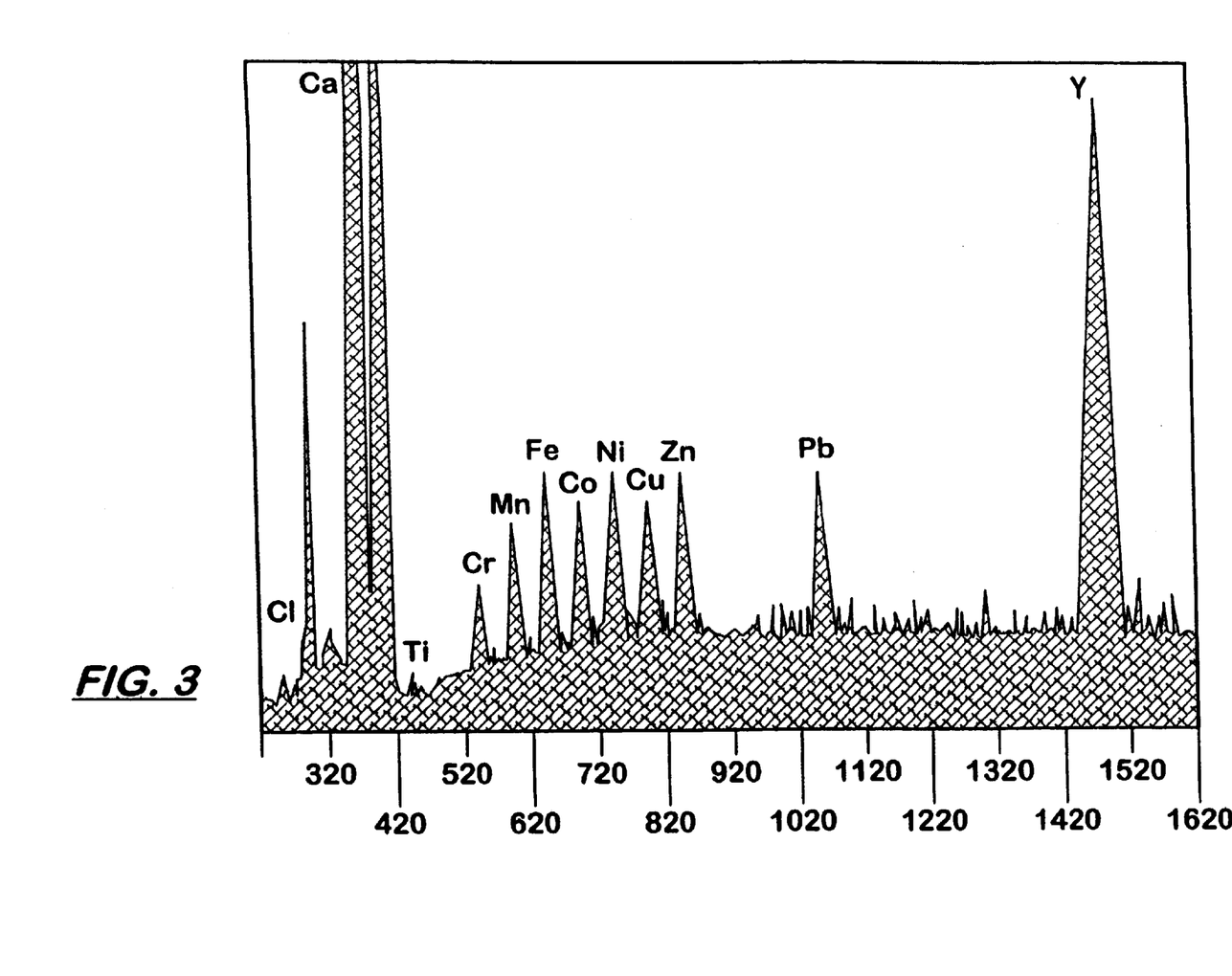

As shown in FIG. 3, the x-rays which are detected have various energies, e.g., there is a broad band of scattered x-rays with energies less than and greater than those of the exciting atom. FIG. 3 illustrates this spectrum for paper as the target material. Within this broad band, there are peaks due to the excitation of the taggant(s) in the sample. The ratio of the intensity of the radiation in any peak to the intensity of the background at the same energy (known as the peak-to-background ratio) is a measure of the concentration of the element which has characteristic X-rays at the energy of that peak, e.g., the taggant.

In one aspect of the detection method of the present invention, at least one target material believing to contain known concentrations of the taggant(s) of interest is selected. The XRF analysis is performed on that target material (or a sample thereof) using a detection device or apparatus containing an x-ray radiation source ("source"), x-ray radiation detector ("detector"), support means, analyzer means, and calibration means.

Figure 4A:
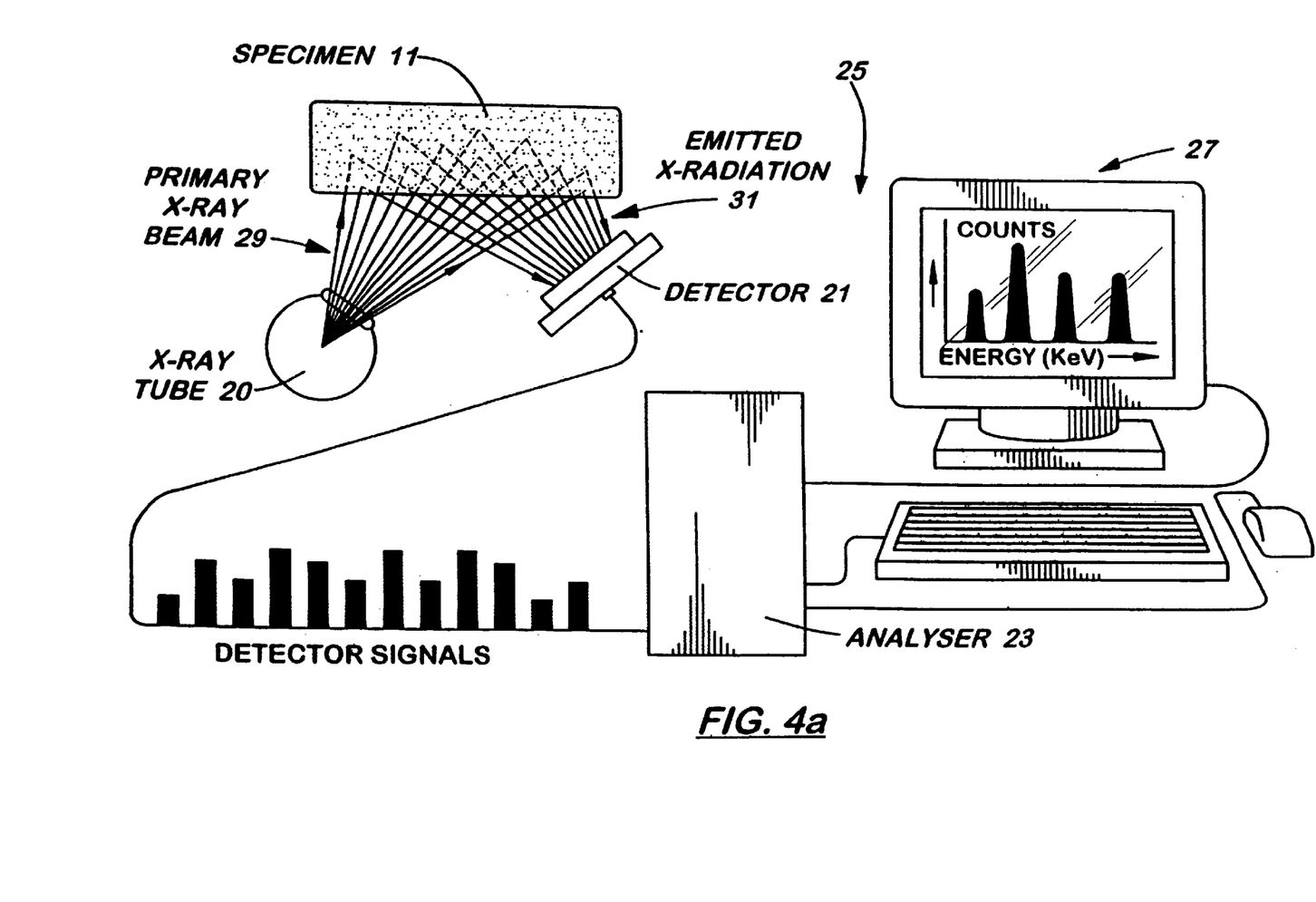

One aspect of the detection device of the present invention is illustrated in FIG. 4a. In this Figure, the detection apparatus 25 has an ordinary x-ray fluorescence spectrometer capable of detecting elements present in a coating, package or material. X-rays 29 from a source (e.g., either x-ray tube or radioactive isotope) 20 impinge on a sample 11 which absorbs the radiation and emits x-rays 31 to an x-ray detector 21 and analyzer 23 capable of energy or wavelength discrimination. This is accomplished by using a commercially available x-ray spectrometer such as an Edax DX-95 or a MAP-4 portable analyzer, commercially available from Edax Inc., Mahwah, N.J. Part of analyzer 23 includes a computerized system 27.

Figure 4B:
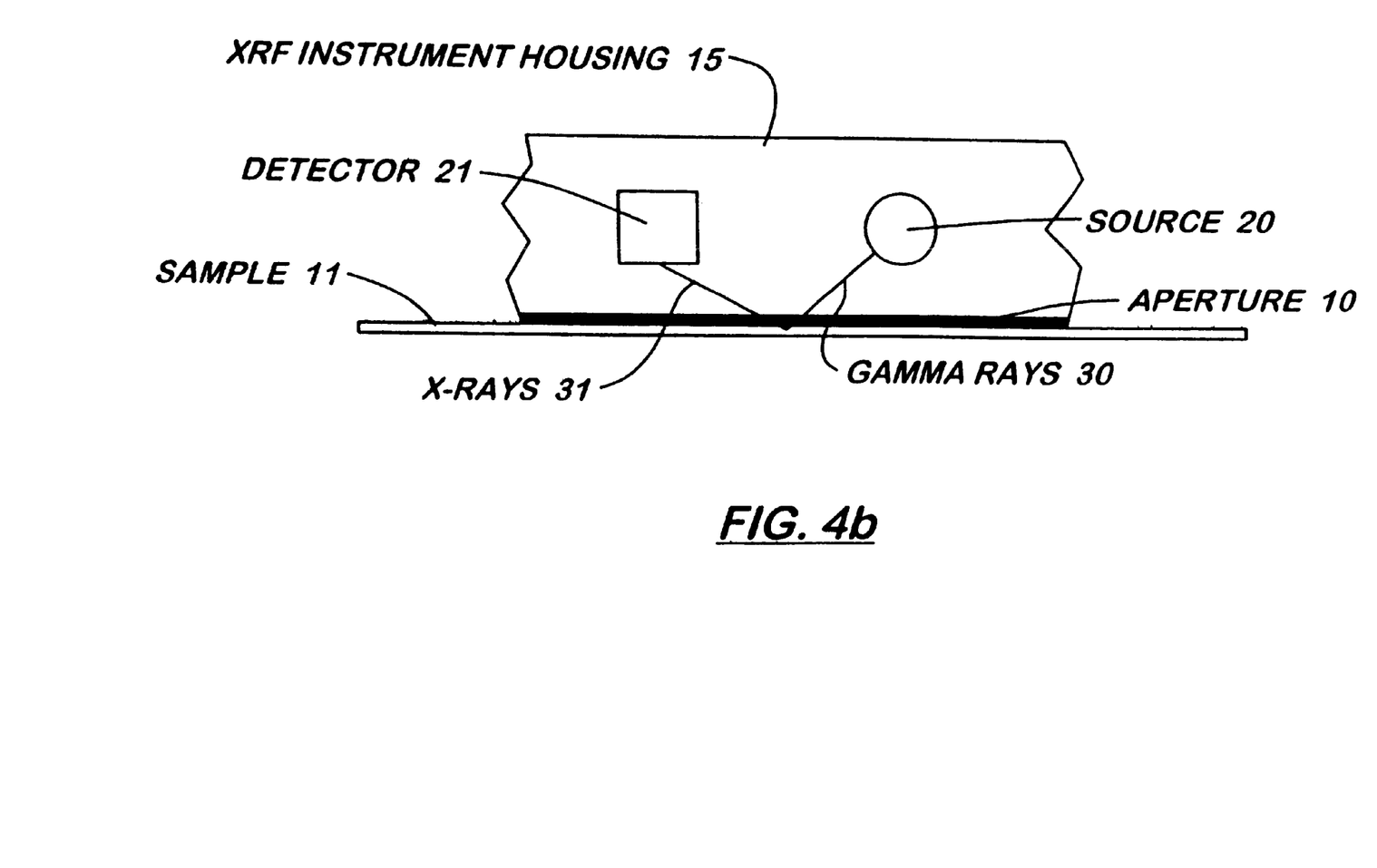

Another aspect of the detection apparatus of the present invention is illustrated in FIG. 4b. In this Figure, the detection apparatus 25 has an instrument housing 15 which contains the various components. Gamma rays or x-rays 30 from a source (e.g., either x-ray tube or radioactive isotope) 20 are optionally focused by aperture 10 to impinge on a sample 11. Sample 11 contains the at least one taggant which absorbs the radiation and emits x-rays 31 to an x-ray detector 21. Optionally, analyzing means can be incorporated within housing 15.

The present invention, however, is not limited to the detection apparatus depicted in FIGS. 4a and 4b. Any suitable source, or plurality of sources, known in the art can be used as the source in the detection device of the present. See, for example, U.S. Pat. Nos. 4,862,143, 4,045,676, and 6,005,915, the disclosures of which are incorporated herein by reference. During the XRF detection process, the source bombards the taggant with a high energy beam. The beam may be an electron beam or electromagnetic radiation such as X-rays or gamma rays. The source, therefore, may be any material which emits such high energy beams. Typically, these have been x-ray emitting devices such as x-ray tubes or radioactive sources.

To target, the beam can be focused and directed properly by any suitable means such as an orifice or an aperture. The configuration (size, length, diameter . . . ) of the beam should be controlled, as known in the art, to obtain the desired XRF detection. The power (or energy level) of the source should also be controlled, as known in the art, to obtain the desired XRF detection.

The source(s) can be shielded and emit radiation in a space limited by the shape of the shield. Thus, the presence, configuration, and the material used for shielding the source should be controlled for consistent XRF detection. Any suitable material and configuration for that shield known in the art can be employed in the present invention. Preferably, any high-density materials used as the material for the shield, e.g, tungsten or brass.

Any suitable detector, or plurality of detectors, known in the art can be used as the detector in the detection device of the present invention. See, for example, U.S. Pat. Nos. 4,862,143, 4,045,676, and 6,005,915, the disclosures of which are incorporated herein by reference. Any type of material capable of detecting the photons omitted by the taggant may be used. Silicon and CZT (cadmium-zinc-telluride) detectors have been conventionally used, but others such as proportional counters, germanium detectors, or mercuric iodide crystals can be used.

Several aspects of the detector should be controlled to obtain the desired XRF detection. First, the geometry between the detector and the target material should be controlled. The XRF detection also depend on the presence, configuration, and material—such as tungsten and beryllium—used as a window to allow x-rays photons to strike the detector. The age of the detector, voltage, humidity, variations in exposure, and temperature can also impact the XRF detection and, therefore, these conditions should be controlled.

The analyzer means sorts the radiation detected by the detector into one or more energy bands and measures its intensity. Thus, any analyzer means performing this function could be used in the present invention. The analyzer means can be a multi-channel analyzer for measurements of the detected radiation in the characteristic band and any other bands necessary to compute the value of the characteristic radiation as distinct from the scattered or background radiation. See, for example, U.S. Pat. Nos. 4,862,143, 4,045,676, and 6,005,915, the disclosures of which are incorporated herein by reference.

The XRF also depends on the resolution of the x-rays. Background and other noise must be filtered from the x-rays for proper measurement, e.g., the signals must be separated into the proper number of channels and excess noise removed. The resolution can be improved by cooling the detector using a thermoelectric cooler—such as a nitrogen or a peltier cooler—and/or by filtering. Another way to improve this resolution is to use pre-amplifiers.

The support means supports the source and detector in predetermined positions relatively to a sample of the target material to be irradiated. Thus, any support means performing this function could be used in the present invention. In one example, the support means comprises two housings, where the source and detector are mounted in a first housing which is connected by a flexible cable to a second housing in which the analyzer means is positioned as illustrated in FIG. 4a. If desired, the first housing may then be adapted to be hand-held. In another example, the source and detector as well as the other components of the detection device are mounted in a single housing as illustrated in FIG. 4b.

The calibration means are used to calibrate the detection apparatus, thus insuring accuracy of the XRF analysis. In this calibration, the various parameters that could be modified and effect the measurement are isolated and calibrated. For example, the geometrical conditions or arrangements can be isolated and calibrated. In another example, the material matrix are isolated and calibrated. Preferably, internal (in situ) calibration during detection is employed as the calibration means in the present invention. Components, such as tungsten shielding, are already present to internally calibrate during the XRF analysis. Other methods, such as fluorescence peak or Compton backscattering, could be used for internal calibration in the present invention.

Analyzer means, which includes a computerized system 27, is coupled to, receives, and processes the output signals produced by detector 21. The energy range of interest, which includes the energy levels of the secondary x-ray photons 44 emitted by the taggant(s), is divided into several energy subranges. Computerized system 27 maintains counts of the number of X-ray photons detected within each subrange using specific software programs, such as those to analyze the detection and x-ray interaction and to analyze backscatter data. After the desired exposure time, computerized system 27 with display menus stops receiving and processing output signals and produces a graph of the counts associated with each subrange.

Figure 5:
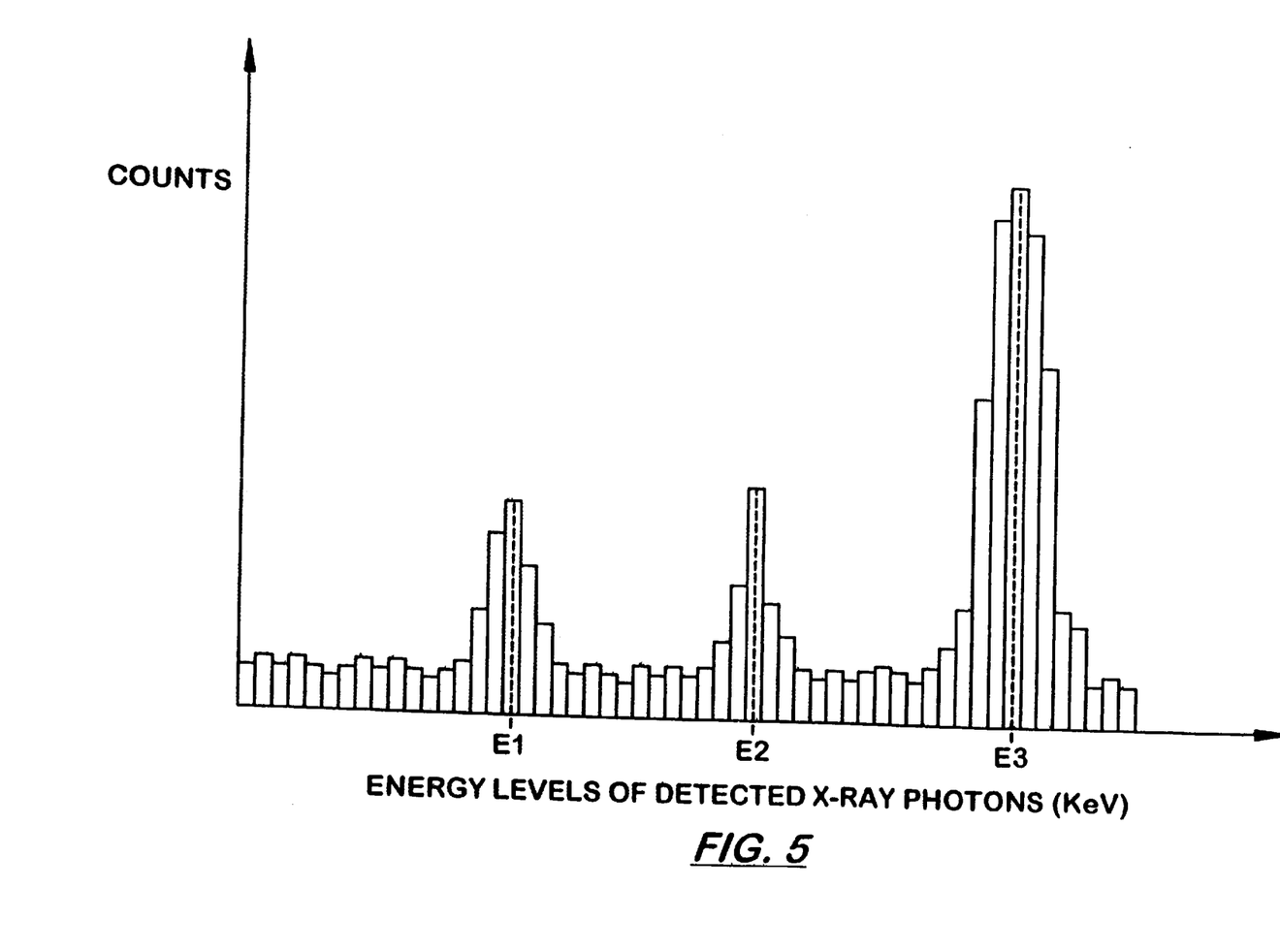

FIG. 5 is a representative graph of the counts associated with each subrange. This graph is essentially a histogram representing the frequency distribution of the energy levels E1, E2, and E3 of the detected x-ray photons. Peaks in the frequency distribution (i.e., relatively high numbers of counts) occur at energy levels of scattered primary x-ray photons as well as the secondary x-ray photons from the taggant(s). A primary x-ray photon incident upon a target material may be absorbed or scattered. The desired secondary x-ray photons are emitted only when the primary x-ray photons are absorbed. The scattered primary x-ray photons reaching the detector of the system create an unwanted background intensity level. Accordingly, the sensitivity of XRF analysis is dependent on the background intensity level, and the sensitivity of XRF detection may be improved by reducing the amount of scattered primary x-ray photons reaching the detector. The peak occurring at energy levels of scattered primary x-ray photons is basically ignored, while the other peaks—those occurring at E1, E2, and E3—are used to identify the at least one taggant present in the target material.

Besides the parameters described above, at least two other parameters must be controlled during the process of XRF detection. First, the media (such as air) through which the gamma rays (and x-rays) must travel also impacts the XRF. Therefore, the different types of media must be considered when performing the XRF analysis. Second, the methods used to interpret and analyze the x-rays depend, in large part, on the algorithms and software used. Thus, methods must be adopted to employ software and algorithms that will consistently perform the XRF detection.

These two parameters, plus those described above, must be carefully accounted for and controlled to obtain accurate measurements. In one aspect of the intention, these parameters could be varied and controlled to another provide a distinct code. For example, using a specific source and a specific detector with a specific measuring geometry and a specific algorithm could provide one distinct code. Changing the source, detector, geometry, or algorithm could provide a whole new set of distinct codes.

Figure 6:
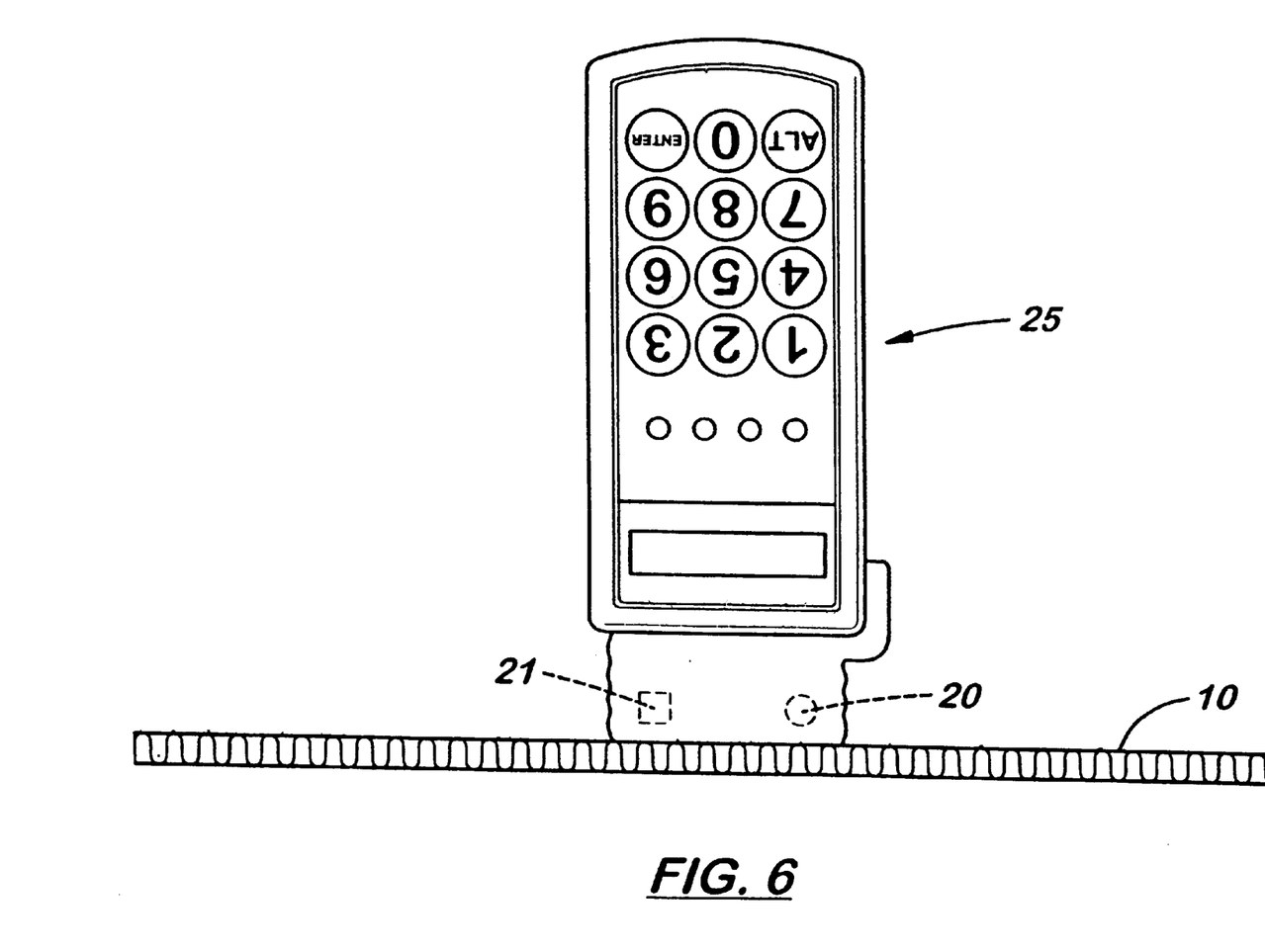

FIG. 6 illustrates a preferred apparatus and detection method according to the present invention. In this Figure, detection apparatus 25 is capable of detecting at least one taggant present in target material 10, such as a document. Detection apparatus 25 is a portable device which can be small enough to be hand-held. Detection apparatus 25 contains all the components discussed above (i.e., source, detector, analyzer means, and calibration means) in a single housing, thus allowing the portability and smaller size.

The present invention is not limited to any specific XRF analysis. Any type of XRF, such as total reflection x-ray fluorescence (TXRF), can be employed in the present invention.

In one aspect of the invention, the apparatus and method used identify an article once it has been tagged. The ability to invisibly tag an article and read the tag, especially through a non line-of-sight method, would provide an invaluable asset in any industry that authenticates, verifies, tracks, labels, or distributes goods of any kind. Indeed, having an invisible taggant(s) could further prevent copying and counterfeiting of goods. In another aspect of the invention, the apparatus and method of the present invention could be used for these same purposes, but for those products that have the desired taggant already located therein. Thus, the present inventions could analyze liquid flows for contaminant particles or pinpoint via 3-D analysis the exact location of a contaminant(s) in an article.

The following non-limiting example illustrates the present invention.

EXAMPLE

A conventional computer system containing a laser printer was obtained. A document was then prepared and printed using the computer system and the laser printer. A table-top detection apparatus, similar to a flat bed scanner, to was used to analyze the document using XRF analysis. The XRF spectra showed no constituents sensitive to the XRF analyzer. This was expected since paper contains only light (low Z) elements which are not sensitive to the XRF detection apparatus.

The detection apparatus contained several components. A trigger actuated tungsten shutter block containing an Iron 55 gamma ray point source and a silicon pin x-ray detector were located within the front of the instrument. Circuit boards, necessary for acquiring and processing the data from the detector were located within the rest of the housing. The instrument had a red and a green light to indicate whether the sample was tagged or not and a read out to inform the user that the sample was tagged. A keypad on the top of the instrument allowed the user to turn the electronics of the instrument on and off, while a key operated lock on the side of the instrument kept the user from inadvertently opening the shutter block, exposing the radioactive source.

The toner cartridge was then removed from the laser printer and opened. A teaspoon of $ZrO_2$ powder was added to the toner cartridge, which contained about two pounds toner. The $ZrO_2$ powder was finer (smaller in particle size) than the toner powder. The toner powder and $ZrO_2$ powder were mixed until a homogenous mixture was obtained. The "tagged" cartridge was then closed and replaced in the laser printer.

Figure 7:
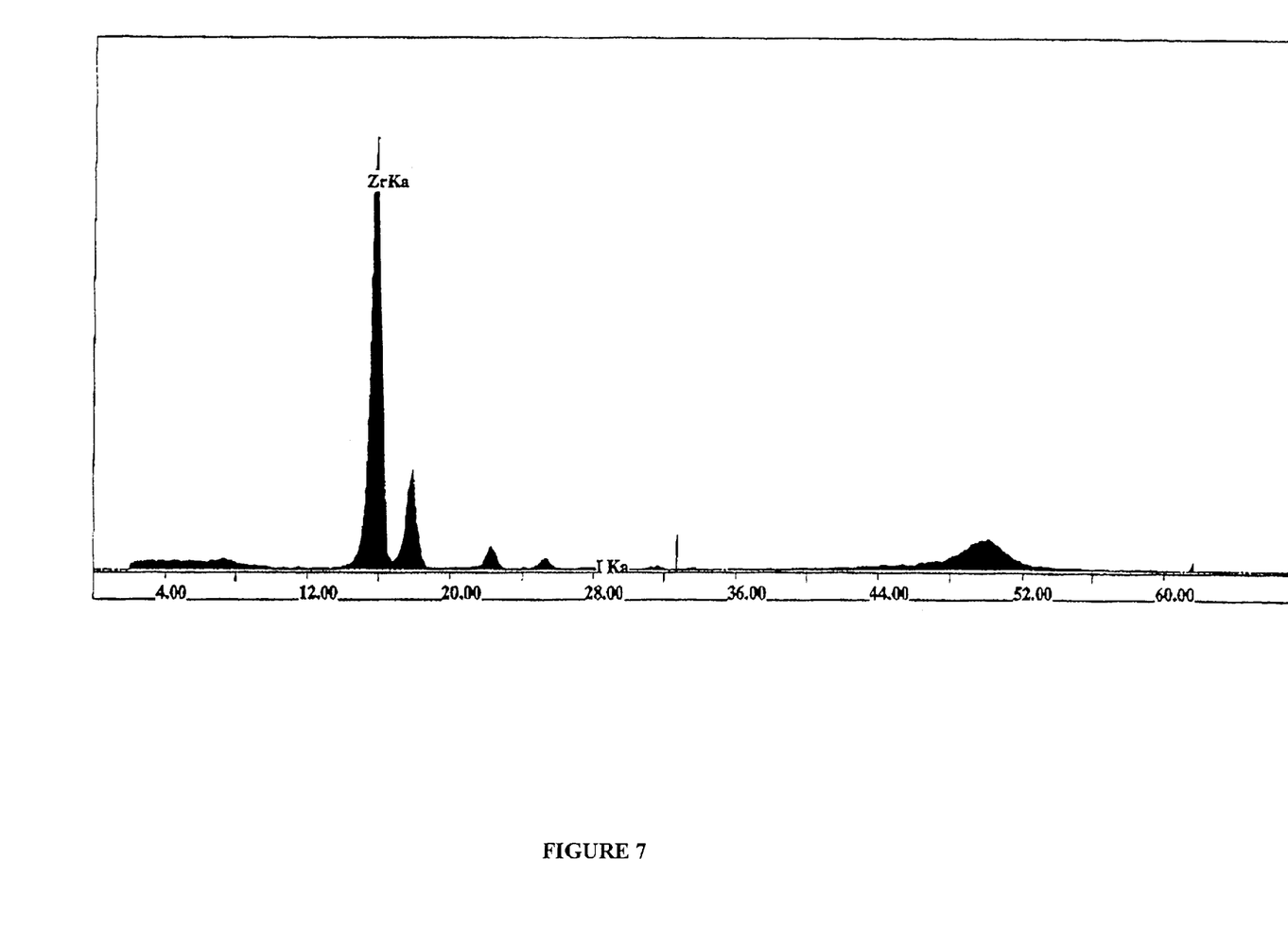

The same document was then printed using the tagged cartridge to make a "tagged" document. The tagged document appeared substantially identical to the un-tagged document in terms of the visual and physical properties. The tagged document was then detected using the same detection apparatus. The spectra of the tagged document is illustrated in FIG. 7, with a prominent peak present for the Zr taggant which was not present in the spectra for the un-tagged document.

Having described the preferred aspects of the present invention, it is understood that the invention defined by the appended claims is not to be limited by particular details set forth in the above description, as many apparent variations thereof are possible without departing from the spirit or scope thereof.

We claim:

1. A method for detecting a taggant in an article, comprising:
   providing a taggant in a portion of an article;
   causing the taggant to radiate an x-ray that penetrates through the portion of the article; and
   analyzing through that portion whether the x-ray has a specific energy.

2. The method of claim 1, wherein the article is a document.

3. The method of claim 1, including providing the taggant in a concentration less than 100 ppm.

4. The method of clam 1, including providing a plurality of taggants with different concentrations.

5. A method for using an article containing a taggant, comprising:
   providing an article with a taggant in a portion thereof;
   causing the taggant to radiate an x-ray that penetrates through the portion of the article; and
   analyzing through that portion whether the x-ray has a specific energy.

6. The method of claim 5, wherein the article is a document.

7. The method of claim 5, including providing the taggant in a concentration less than 100 ppm.

8. The method of claim 5, including providing a plurality of taggants with different concentrations.

9. A method for using a coating containing a taggant, comprising:
   providing a coating with a taggant in a portion thereof;
   impinging the taggant with an x-ray to cause the taggant to radiate an x-ray that penetrates through the portion of the coating; and
   analyzing through that portion whether the radiated x-ray has a specific energy.

10. The method of claim 9, wherein the coating comprises ink.

11. The method of claim 9, including providing the taggant in a concentration less than 100 ppm.

12. The method of claim 9, including providing a plurality of taggants with different concentrations.

13. A method for detecting a taggant in an article, comprising:
   providing a taggant in a non-visible portion of an article;
   causing the taggant to radiate an x-ray; and
   analyzing whether the x-ray has a specific energy.

14. The method of claim 13, wherein the article is a document.

15. The method of claim 13, including providing the taggant in a concentration less than 100 ppm.

16. The method of claim 13, including providing a plurality of taggants with different concentrations.

17. A method of making an article containing a taggant, comprising:
   providing a non-visible portion of an article; and
   providing that portion with a taggant that radiates an x-ray when an energy beam is impinged on the taggant.

18. The method of claim 17, wherein the article is a document.

19. The method of claim 17, including providing the taggant in a concentration less than 100 ppm.

20. The method of claim 17, including providing a plurality of taggants with different concentrations.

21. A coating for an article, the coating comprising a non-visible portion with a taggant therein which radiates an x-ray when an energy beam is impinged on the taggant.

22. The method of claim 21, wherein the coating comprises ink.

23. The coating of claim 21, including providing the taggant in a concentration less than 100 ppm.

24. The coating of claim 21, including providing a plurality of taggants with different concentrations.

25. An article containing a taggant made by the method comprising:
   providing a non-visible portion of the article; and
   providing a taggant in the portion of the article, the taggant radiating an x-ray when an energy beam is impinged on the taggant.

26. The article of claim 25, wherein the article is a document.

27. The article of claim 25, including providing the taggant in a concentration less than 100 ppm.

28. The article of claim 25, including providing a plurality of taggants with different concentrations.

29. An article comprising a taggant in a non-visible portion thereof, the taggant radiating an x-ray when an energy beam is impinged on the taggant.

30. The article of claim 29, wherein the article is a document.

31. The article of claim 29, including providing the taggant in a concentration less than 100 ppm.

32. The article of claim 29, including providing a plurality of taggants with different concentrations.

33. A method of tagging an article with a taggant comprising:

providing a non-visible portion of the article; and providing a taggant in that portion of the article, the taggant radiating an x-ray when an energy beam is impinged on the taggant.

34. The method of claim 33, wherein the article is a document.

35. A method for using an article containing a taggant, comprising:

providing an article with a taggant in a non-visible portion thereof;

causing the taggant to radiate an x-ray; and analyzing whether the x-ray has a specific energy.

36. The method of claim 35, wherein the article is a document.

37. A method of tagging a coating for an article comprising:

providing a coating on a portion of an article; and providing a taggant in a non-visible portion of the coating, the taggant radiating an x-ray when an energy beam is impinged on the taggant.

38. The method of claim 37, wherein the article is a document.

39. The method of claim 37, including providing the taggant in a concentration less than 100 ppm.

40. The method of claim 37, including providing a plurality of taggants with different concentrations.

41. A method for using a coating containing a taggant, comprising:

providing a coating containing a non-visible portion with a taggant therein;

causing the taggant to radiate an x-ray; and analyzing whether the x-ray has a specific energy.

42. The method of claim 41, wherein the coating comprises ink.

43. The method of claim 41, including providing the taggant in a concentration less than 100 ppm.

44. The method of claim 41, including providing a plurality of taggants with different concentrations.

* * * * *